US008110157B2

(12) United States Patent
Lepschi et al.

(10) Patent No.: US 8,110,157 B2
(45) Date of Patent: Feb. 7, 2012

(54) HEATED REACTION CHAMBER FOR PROCESSING A BIOCHIP AND METHOD FOR CONTROLLING SAID REACTION CHAMBER

(75) Inventors: Jana Lepschi, Jena (DE); Jens Gohring, Jena (DE); Stefan Heydenhaus, Erfurt (DE); Manuel Ullrich, Unterwellenborn (DE)

(73) Assignee: Zenteris GmbH, Jena (DE)

( * ) Notice: Subject to any disclaimer, the term of this patent is extended or adjusted under 35 U.S.C. 154(b) by 273 days.

(21) Appl. No.: 12/306,299

(22) PCT Filed: Jun. 27, 2007

(86) PCT No.: PCT/EP2007/056430

§ 371 (c)(1),
(2), (4) Date: Feb. 6, 2009

(87) PCT Pub. No.: WO2008/000770

PCT Pub. Date: Jan. 3, 2008

(65) Prior Publication Data

US 2009/0197778 A1 Aug. 6, 2009

(30) Foreign Application Priority Data

Jun. 27, 2006 (DE) ......................... 10 2006 030 378
Jun. 27, 2006 (DE) ......................... 10 2006 030 379
Jun. 27, 2006 (DE) ......................... 10 2006 030 380
Jun. 27, 2006 (DE) ......................... 10 2006 030 381

(51) Int. Cl.
*G01N 33/00* (2006.01)

(52) U.S. Cl. ........................ 422/430; 422/401; 422/68.1

(58) Field of Classification Search .................. 422/430, 422/401, 68.1
See application file for complete search history.

(56) References Cited

U.S. PATENT DOCUMENTS 4,695,709 A 9/1987 Sachs et al.
4,720,372 A 1/1988 Fey et al.
5,105,067 A 4/1992 Brekkestran et al.
5,552,998 A 9/1996 Datta
7,501,301 B2 * 3/2009 Kovacs et al. .................. 438/49

FOREIGN PATENT DOCUMENTS

DE 102004022263 A1 12/2005

OTHER PUBLICATIONS

International Search Report for PCT/EP2007/056430 mailed Nov. 14, 2007, three pages.
Shen et al. "A microchip-based PCR device using flexible printed circuit technology," Sensors and Actuators B 105 (2005) pp. 251-258.

* cited by examiner

*Primary Examiner* — Sam P Siefke
(74) *Attorney, Agent, or Firm* — Rankin, Hill & Clark LLP

(57) ABSTRACT

The invention relates to a heated reaction chamber for processing a biochip and to a method for controlling said reaction chamber. The heated reaction chamber for processing a biochip comprises a chamber wall, constituted by a flexible circuit board (10), a circuit path (10.3) being configured on the flexible circuit board (10) and being used as the heating device. The use of a flexible circuit board as the wall of a reaction chamber allows for a low thermal capacity of the reaction chamber in the area of the heating device, thereby allowing the chamber to be heated up quickly.

29 Claims, 20 Drawing Sheets

HEATED REACTION CHAMBER FOR PROCESSING A BIOCHIP AND METHOD FOR CONTROLLING SAID REACTION CHAMBER

The invention relates to a heated reaction chamber for processing a biochip and to a method for controlling said reaction chamber.

A biochip comprises a usually planar substrate with various catcher molecules disposed in predetermined locations—the spots—on the surface of the substrate. A marked sample substance reacts with certain catcher molecules in accordance with the key-and-lock principle. The catcher modules usually consist of DNA sequences (see e.g. EP 373 203 B1) or proteins. Such biochips are also referred to as arrays or DNA arrays. They are often marked using fluorescence markers. The fluorescence intensity of the individual spots is detected with an optical reader. This intensity correlates with the number of the marked sample molecules immobilised with the catcher molecules.

WO 2005/108604 A2 discloses a heated reaction chamber for processing a biochip. This reaction chamber is provided with an elastic membrane. A silicon biochip is located on the membrane. A nickel-chromium thin film conductor is provided as a heating device. Such nickel-chromium thin film conductors have a very high electrical resistance and a correspondingly high heating power. Adjacent to the conductor for the resistance heating system, another conductor is provided for temperature measurement.

In this known reaction chamber (FIG. 10, 11), a housing wall is designed as a membrane, so that the biochip 6 can be pushed against a cover glass 23 located opposite the membrane 13 by means of a plunger 12. As a result, a reaction fluid 26 in the reaction chamber is displaced by the surface of the biochip and does not impede the optical detection. A seal 22 is provided between the membrane 13 and the cover glass 23. The sample fluid 26 enters through a filling cannula 19 pushed through the seal 22. As the plunger is operated, surplus sample fluid 26 is discharged from the reaction chamber 5 by means of a pressure balancing cannula 20.

WO 01/02 094 A1 describes means for tempering biochips which include micro-structured resistance heating lines.

U.S. Pat. No. 5,759,846 and U.S. Pat. No. 6,130,056 describe reaction chambers for the accommodation of biological tissues. A flexible printed circuit board with electrodes is provided in the reaction chamber. By compressing the biological tissue and the flexible printed circuit board, an electrical contact can be established between the biological tissue and the electrodes of the flexible printed circuit board, to that a current can be tapped directly at the biological tissue.

DE 10 2005 09 295 A1 describes a chemical reaction cartridge with a plurality of chambers. By rolling a roller along the surface of the cartridge, fluids can be transferred from one chamber to another chamber. In addition, a metal rod is provided, by means of which pressure, vibrations, heat, coolness or the like can be applied to the cartridge to accelerate the chemical reaction within the cartridge.

From K. Shen et al., Sensors and Actuators B105 (2005), pages 251-258, "A microchip-based PCR device using flexible printed circuit technology", the use of a flexible printed circuit board for heating a reaction chamber provided for a PCR process is known. The reaction chamber comprises a glass plate, a frame and a plastic cover. The flexible printed circuit board is mounted on the outside of the glass plate, either directly by means of bonding or by means of a copper chip located in between. Owing to the good thermal properties of the flexible printed circuit board, heating rates of 8° C./s were achieved. A conductor formed on the flexible printed circuit board is used both for heating and for temperature measurement. The heating process is carried out in a "heating state" and the measuring process in a "sensing state", with a time offset between the two processes.

The invention is based on the problem of creating a simple and cost-effective heated reaction chamber for processing a biochip, which can be heated very efficiently and which allows for the operation of a plunger as known from WO 2005/108604 A2. The invention is further based on the problem of creating a method for controlling said reaction chamber.

This problem is solved by a heated reaction chamber with the features of claim 1 and by a method with the features of claim 21. Advantageous further developments of the invention are specified in the respective dependent claims.

The heated reaction chamber according to the invention for processing a biochip comprises a chamber wall represented by a flexible printed circuit board. A conductor serving as a heating device, which is hereinafter referred to a heating conductor, is formed on the flexible printed circuit board. On the one hand, the flexible printed circuit board serves as a flexible membrane which can be operated by a plunger to push a biochip mounted thereon against a window of the reaction chamber located opposite. On the other hand, the flexible printed circuit board serves as a heating device, because the heating conductor mounted thereon carries a heating current which generates heat to be transferred to the reaction chamber.

As the heating conductor has a meandering shape, it evenly covers a predetermined surface area, having a constant thickness and width along its entire length. The heating conductor may also be designed as a double spiral. The conductor is advantageously designed without crossovers, so that it can be made from a copper layer.

As the flexible printed circuit board combines two functions (elastic membrane, heating device), a component can be omitted compared to conventional heated reaction chambers for processing a biochip. This results in a considerable reduction of the thermal capacity in the region of the chamber wall where the heating device is provided. This makes the heat transfer to the biochip significantly more efficient than in known heated reaction chambers. In this context, it has to be taken into account that flexible printed circuit boards are very thin as a matter of principle and have a low thermal capacity.

According to a preferred embodiment, the heated reaction chamber comprises a measuring and control unit which is designed such that the single heating conductor of the flexible printed circuit board is used both for heating and for measuring the temperature. This allows the conductor, in the region where the biochip in the reaction chamber rests on the flexible printed circuit board, to be routed in evenly meandering loops, so that the entire surface of the biochip is evenly heated.

The measuring device comprises two preferably identical measuring channels designed for measuring the current or the voltage at the conductor serving as a heating device. As both the current and the voltage at the heating conductor are measured, the heating conductor can be used both for measuring and for heating, because the current can be varied in accordance with the required heating power.

The heating conductor provided as a heating device on the flexible circuit board has a resistance of approximately 5 to 10 ohms at room temperature.

The heating conductor on the flexible printed circuit board is preferably made of copper, because copper conductors can be produced both cost-effectively and with great precision.

The copper heating conductor preferably has a purity of at least 99%, as the temperature coefficient of pure copper is very constant in the temperature range which is relevant here.

The voltage of the conductor serving as a heating device is preferably measured in a four-point-process.

The flexible printed circuit board may comprise two conductive layers, one forming the conductor for heating and the other being a flat layer, in particular a copper layer, covering the entire heated region, so that the generated heat is distributed quickly and evenly over the entire surface to be heated.

According to the method according to the invention for controlling the heated reaction chamber, the heating conductor of the flexible printed circuit board is supplied with a heating/measuring current for heating the reaction chamber and for measuring the temperature. There is therefore no need for two separate conductors for heating and temperature measurement in the region to be heated, which enables the conductor to meander evenly across the entire region to be heated.

The temperature is measured with a scanning rate of at least 1000 Hz or approximately 3000 Hz. This allows for a very precise setting of a temperature profile varying with time.

The method for controlling the temperature in the reaction chamber is designed for using a PI controller within a temperature interval about a set temperature and a P controller outside said interval. This avoids an overshooting of the temperature while allowing the quick and precise setting of the set temperature.

The invention is explained below with reference to the embodiments shown in the drawings. Of the drawings.

EMBODIMENT

Figure 1:
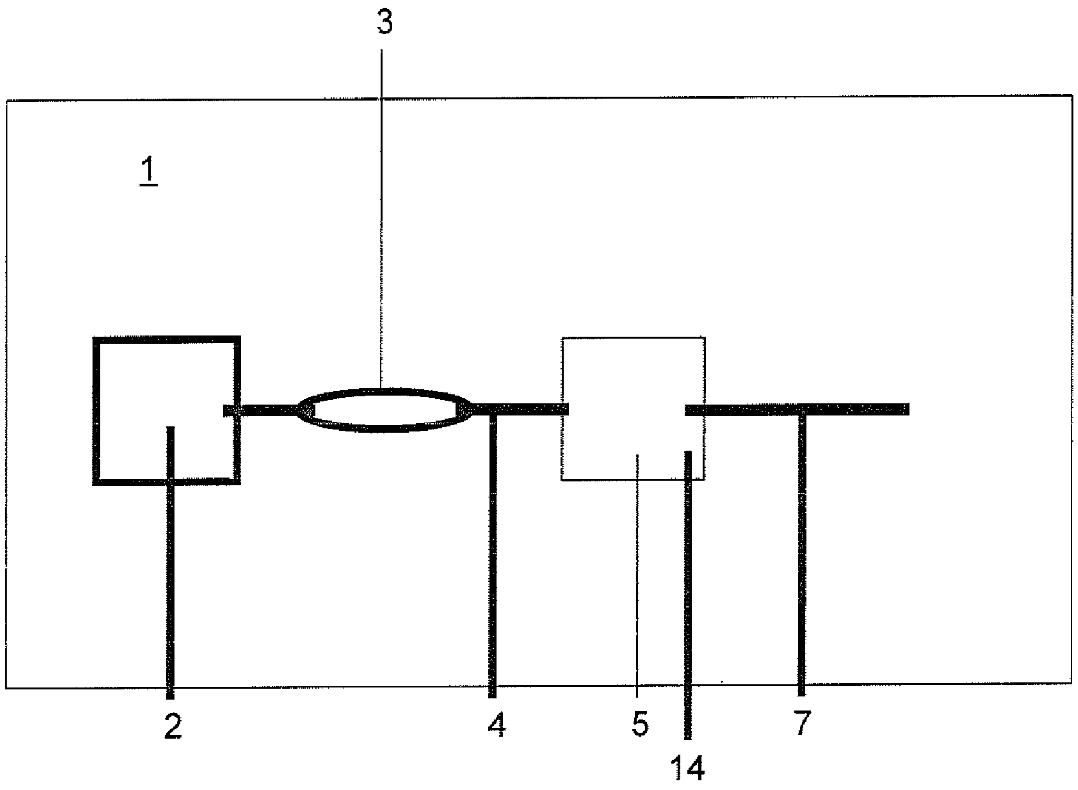
FIG. 1 is a bottom view of a base body of a cartridge according to the invention.
Figure 2:
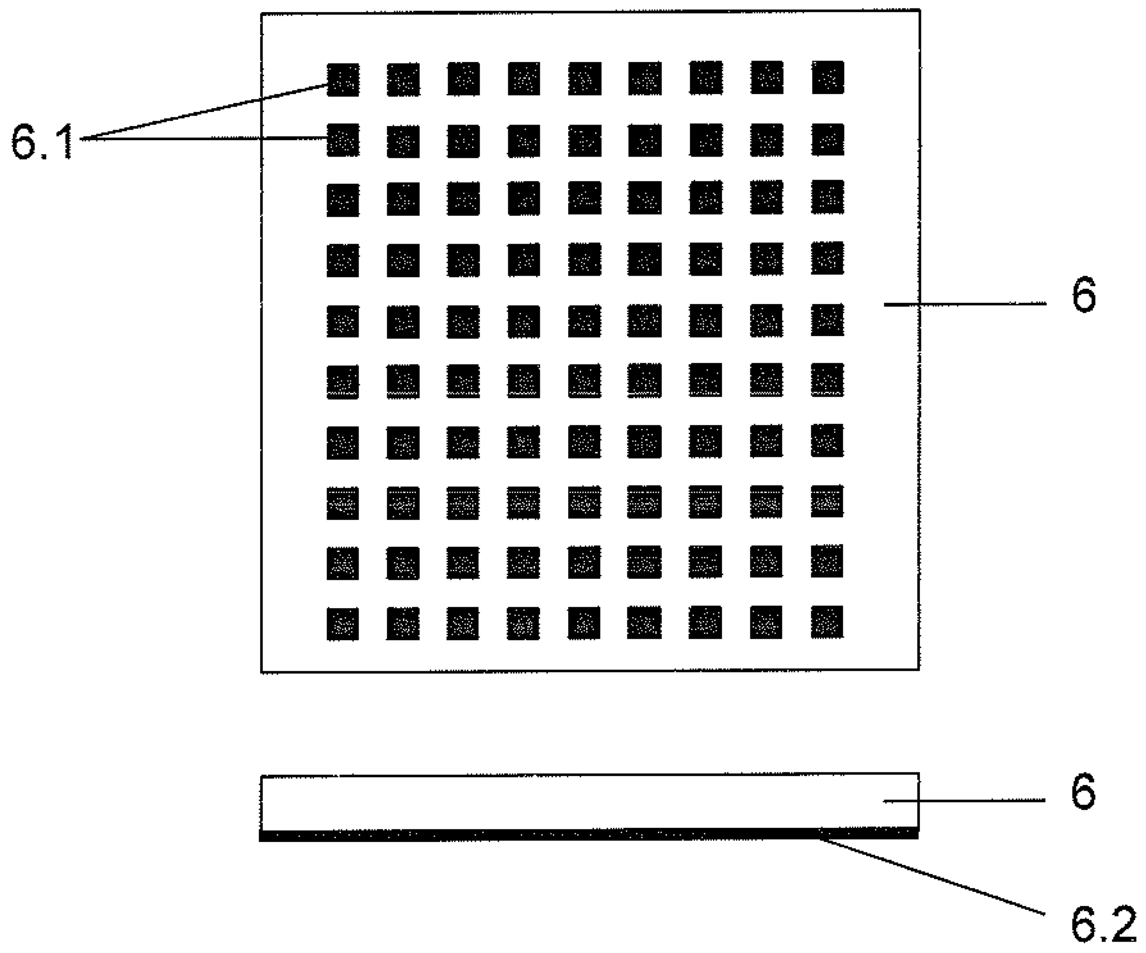
FIG. 2 shows an embodiment of the reaction fields (spots) on a biochip with an optically impermeable and non-fluorescent rear side.

Cartridge:

A cartridge with a biochip is described with reference to FIGS. 1-9 and 12.

A base body 1, which may be injection-moulded from a plastic material, has on its underside a recess for a filling passage 7 leading from a filling port 9 to a reaction chamber 5 (FIG. 1, 6) and recesses for the reaction chamber 5, a equalization passage 4 between the reaction chamber 5 and a equalization chamber 2 and a recess for the equalization chamber 2. The filling port 9 has a tapering section (FIG. 6) which simplifies the introduction of a pipette tip. A check valve 8 is provided in the filling port. The equalization passage 4 has a window 3 through which the presence of a sample fluid in the equalization passage 4 can be detected. The base body 1 is transparent at least in the region of the reaction chamber 5, thus acting as a detection window 14 through which a biochip 6 placed below can be detected.

The connecting passages are kept as short as possible with a cross-section as small as possible in order to obtain a small dead volume and to limit the sample fluid surplus required.

A flexible printed circuit board 10 hereinafter referred to as flexible PCB 10 (FIG. 3) is mounted on the underside of the base body 1. The flexible PCB 10 is so connected to the underside of the base body 1 that the recesses 7, 5, 4, 3, 2 are finite towards the bottom, forming a continuous, communicating and self-contained fluid passage.

Figure 3:
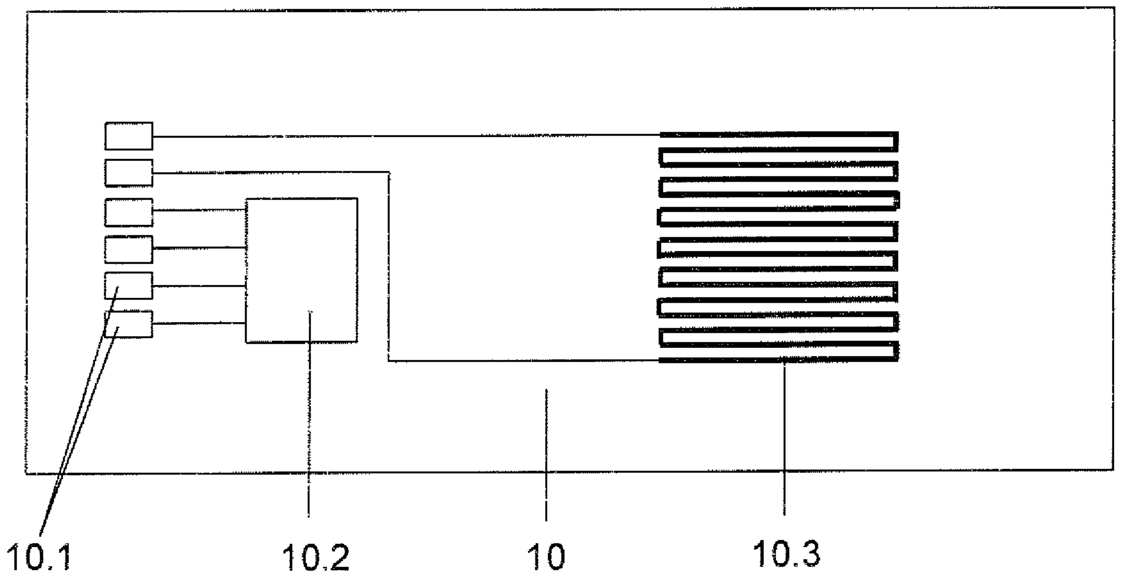
FIG. 3 shows an embodiment of a flexible printed circuit board used according to the invention with an internal heating/measuring structure and integrated EEPROM.

The flexible PCB 10 comprises contact surfaces 10.1, a digital storage medium (e.g. an EEPROM) and an internal heating/measuring structure 10.3 (FIG. 3).

The reaction chamber 5 contains a biochip 6 (FIG. 2) with a number of M-N reaction fields 6.1. To avoid optical retroreflexion and undesirable fluorescence radiation from the flexible PCB 10, the back of the biochip 6 is optically opaque and non-fluorescent, for example coated with chrome black 6.2. The flexible PCB 10 acts as a boundary wall for the reaction chamber 5.

The biochip 6 is first secured to the flexible PCB 10, and the flexible PCB 10 is then joined to the base body 1. The joint between the flexible PCB 10 and the base body 1 is established by means of an adhesive bonding layer 17, for example a suitable adhesive tape (suitable for biological reactions) or a silicone adhesive.

The flexible PCB 10 with the mounted biochip 6 is then adjusted relative to the base body 1 and secured thereto, forming an inlay 11. A durable, heat and water resistant joint can for example be produced using a biologically compatible adhesive tape with a silicone adhesive, or by means of laser welding, ultrasonic welding or other biologically compatible adhesives.

Figure 4:
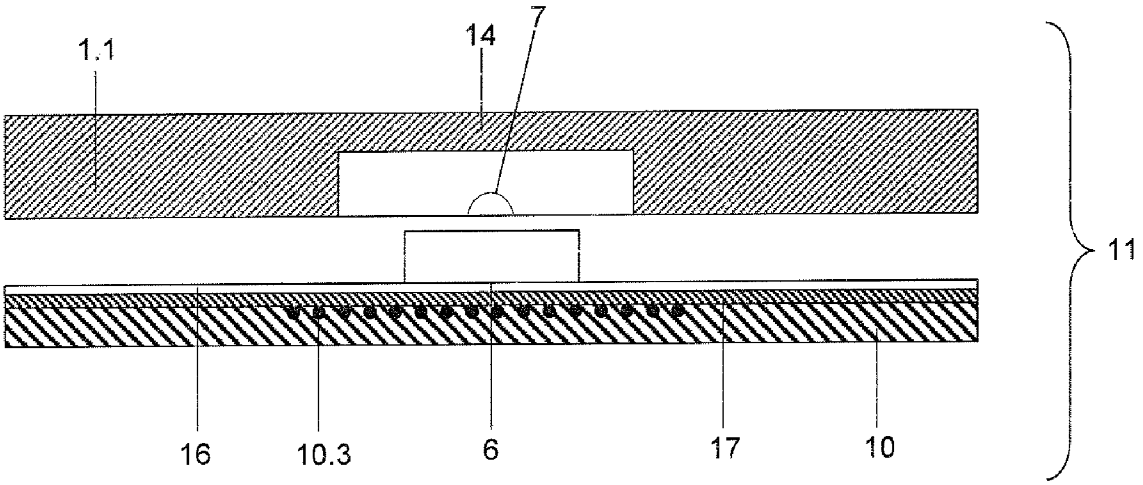
FIG. 4 shows a first embodiment of a biochip with a flexible printed circuit board mounted on a base body.

It is possible to coat the flexible PCB 10 with the adhesive tape (or adhesive) over a large part of its surface, to bond the biochip 6 above the heating/measuring structure 10.3 of the flexible PCB and then to adjust the base body 1 relative to the biochip 6 and to fix the flexible PCB 10 over the entire surface of the base body 1 (FIG. 4).

Figure 5:
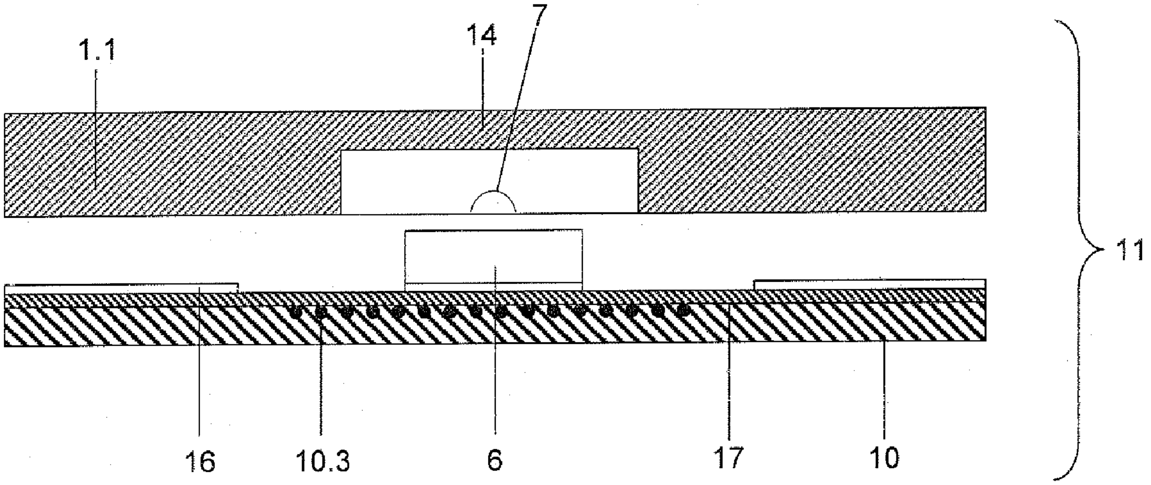
FIG. 5 shows a second embodiment of a biochip with a flexible printed circuit board mounted on a base body.

The flexible PCB 10, the biochip 6 and the base body 1 can alternatively be joined together by bonding targeted areas of the biochip 6 to the flexible PCB 10 (adhesive under the biochip only) followed by the fixing of the base body 1 outside the reaction chamber 5 only (FIG. 5). This type of bonding results in a more efficient heat transfer from the heating/measuring structure 10.3 in the flexible PCB 10 into the reaction chamber 5.

Figure 12:
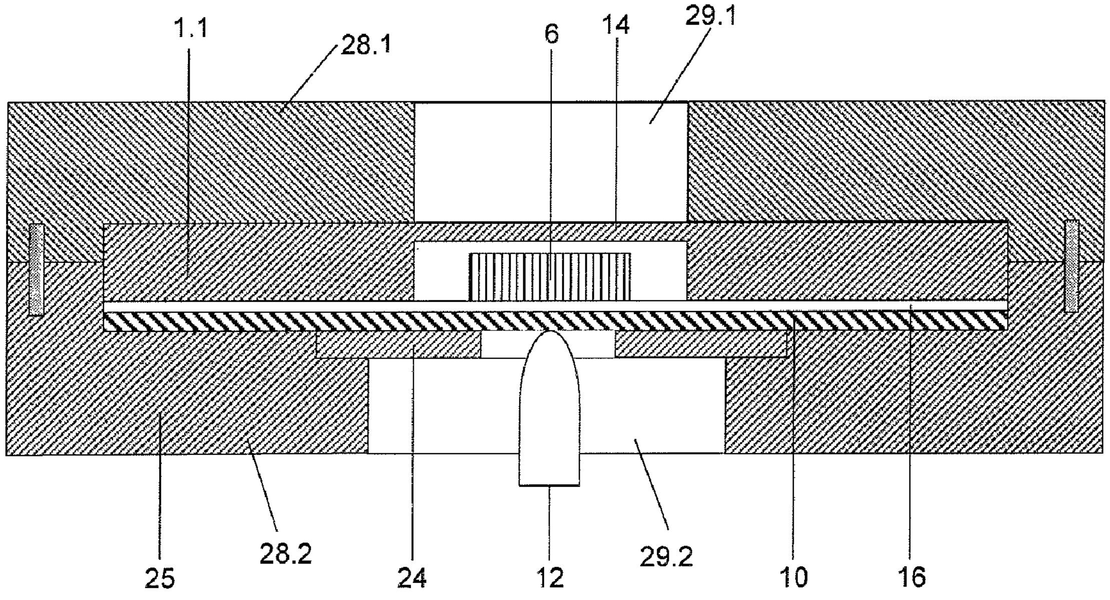
FIG. 12 shows a cartridge with an inlay and a stabilising plate for the flexible printed circuit board.

This pre-assembled inlay 11 comprising base plate, biochip, flexible PCB and check valve is pressed into a cartridge housing 28 for easier handling and stabilisation (FIG. 12). The cartridge housing consists of an upper and a lower part 28.1, 28.2, which bound a rectangular space in which the inlay is positively accommodated. In the region of the reaction chamber 5, the two parts 28.1 and 28.2 of the cartridge housing are provided with approximately rectangular recesses 29.1 and 29.2 respectively. The recess 29.2 of the lower part 28.2 of the cartridge housing may contain a stabilising plate 24, which bears against the flexible PCB 10 of the inlay 11 and has an approximately central opening which is smaller than the recess 29.2 of the lower part 28.2 of the cartridge housing. Whether or not a stabilising plate 24 is useful depends on the pressure level within the reaction chamber 5 and on the degree of deflection of the flexible PCB caused thereby.

Filling Process:

The sample fluid is injected by means of a syringe or pipette at the filling port 9 into the reaction chamber 5 through the check valve 8 and the filling passage 7. The sample fluid initially fills the reaction chamber 5 and then flows into the equalization passage 4 and perhaps into the equalization chamber 2. The quantity is preferably chosen such that no sample fluid enters the equalization chamber 2. During the filling process, a positive pressure develops in the inlay 11, compressing the air in the equalization chamber 2. The fluid level can be observed through the window 3 in the equalization passage 4. As the volumes of the filling passage 7, the reaction chamber 5 and the equalization passage 4 are known, the fluid volume can be kept constant even without observing the optical window.

The pressure-tight seal provided by the check valve 8 generates a positive pressure in the reaction chamber as the cartridge is filled. The air in the equalization chamber is compressed. By varying the volumes of the reaction chamber 5 and the equalization chamber 2, this positive pressure can be adjusted as required. It lies in the range of 0 bar to 1 bar. If the volumes of the reaction chamber and the equalization chamber are equal, the internal pressure doubles in the filling process. Temperatures up to 100° C. can be generated during the temperature-controlled biological test reaction. The thermal expansion of the sample fluid results in its displacement into the equalization passage 4. In the cooling process that sample fluid then retracts. The pressure differentials at $T_{max}$ and $T_{min}$ (in the hot and the cold state) are minimal, as the air in the equalization chamber 2 is compressed. The volume of the equalization chamber significantly exceeds the increase in volume of the sample fluid in the heating process.

The stabilising plate 24 can minimise the expansion of the flexible PCB 10 in the filling process without affecting its ability to push the biochip 6 against the detection window 14 (FIG. 12).

A pressure increase of 1 bar in the cartridge offers the advantage that the boiling point of the sample fluid rises from 100° C. to 125° C. This minimises the formation of air bubbles in the reaction chamber.

Heating Device for Temperature-Controlled Biological Test Reaction:

A temperature-controlled biological test reaction requires the precise adjustment of the temperatures of the sample fluid in the reaction chamber. In carrying out a PCR, for example, temperatures between 30° C. and 98° C. are aimed at. Within the reaction chamber, the temperature of the sample fluid has to be distributed homogeneously, and any temperature changes (heating, cooling) have to be achieved quickly.

The flexible PCB 10 supports a heating/measuring structure which acts as a heating device as current flows through the ohmic resistor. This heats the sample fluid in the reaction chamber to the required temperature T. At the same time, the heating/measuring structure can be used as a temperature sensor by using the resistance characteristic R(T) for the determination of temperature.

The flexible PCB 10 with the integrated heating conductor causes local temperature fluctuations. There are hot spots immediately above the heating/measuring structure. A temperature homogenisation layer 21 (FIG. 7) on the flexible PCB 10 homogenises the temperature distribution on the top of the flexible PCB 10. The temperature homogenisation layer 21 is a copper layer which is nickel-plated and provided with an additional gold coating. The gold offers the advantage of being inert for biological materials, allowing them to come into direct contact with this layer in the reaction chamber. Owing to this, the reaction chamber can also be used for experiments which do not involve biochips. This homogenisation layer has a good thermal conductivity. In place of the copper-nickel-gold combination, a relatively thick copper layer may be provided.

A heating conductor integrated into the flexible PCB has a low inherent thermal capacity. This allows for higher heating rates of the sample fluid in the reaction chamber.

Figure 13:
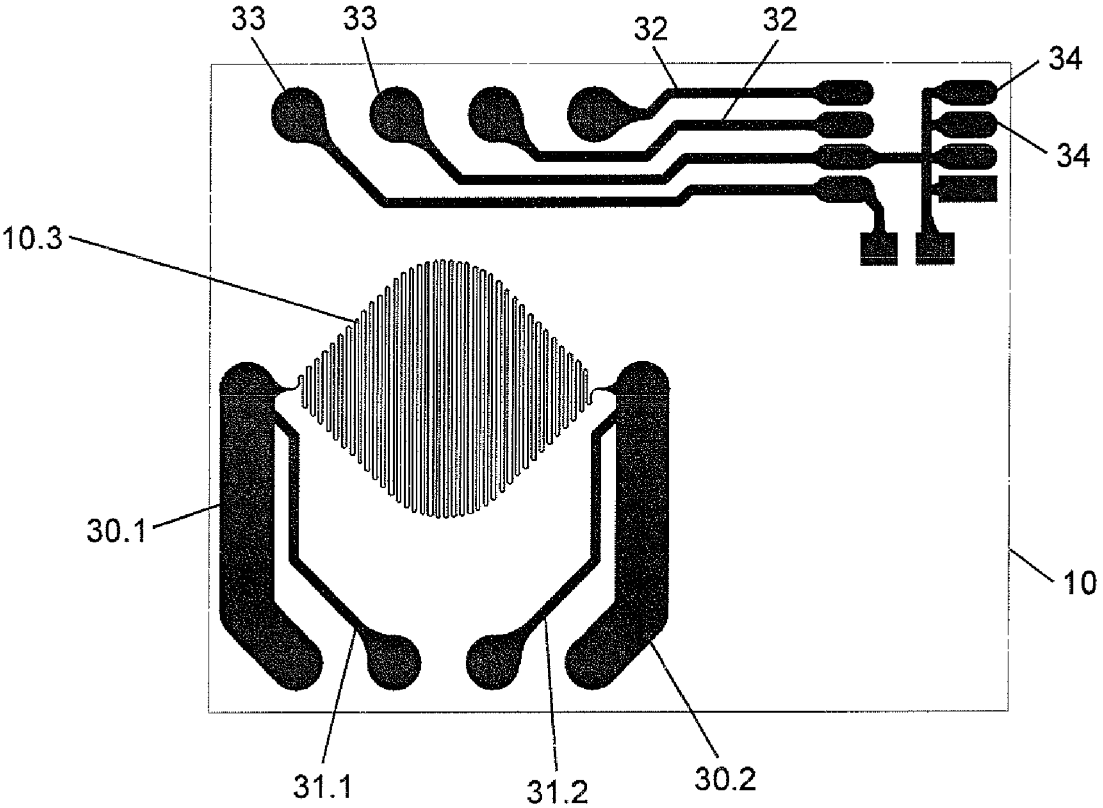
FIG. 13 shows a preferred embodiment of a layout of the flexible printed circuit board.

A preferred embodiment of the layout of the flexible PCB 10 is shown in FIG. 13. The meandering heating/measuring structure 10.3 is made from a thin conductor with a width of 60 μm and a thickness of 16 μm. It is approximately 450 mm long. At room temperature, it has an electrical resistance of approximately 6 to 8 ohms. The conductor is made of copper, preferably of copper with a purity of 99.99%. This pure copper has a temperature coefficient which is nearly constant in the temperature range which is relevant in this context. As a whole, the heating/measuring structure 10.3 has a diamond shape with an edge length of approximately 9 mm. Prototypes of flexible PCBs with a copper layer with a thickness of 5 μm and with structures with a width of 30 μm are already available. With such conductors, a resistance of approximately 100 to 120 ohms could be obtained.

The edge length of the biochip 6 is only 3 mm, so that the diamond shape formed by the heating/measuring structure 10.3 and the temperature homogenisation layer 21 covers a larger area than the biochip.

The end points of the meandering heating/measuring structure merge into very wide conductors 30.1 and 30.2, which supply the heating current and, owing to their width, have only a low resistance. To each of these two conductors 30.1 and 30.2, a further conductor 31.1 and 31.2 respectively is connected in the region of the connecting site of the meandering heating/measuring structure. These two further conductors 31.1 and 31.2 are used for tapping the voltage drop at the heating/measuring structure. This will be explained in greater detail below.

The flexible PCB 10 has conductors 32 and corresponding contact points 33, 34 for the connection of an electric semiconductor memory. This semiconductor memory is used for storing calibration data for the heating device and the data of the biological experiments to be conducted with the biochip of the cartridge. These data are stored in a way which protects against mistakes.

Figure 14:
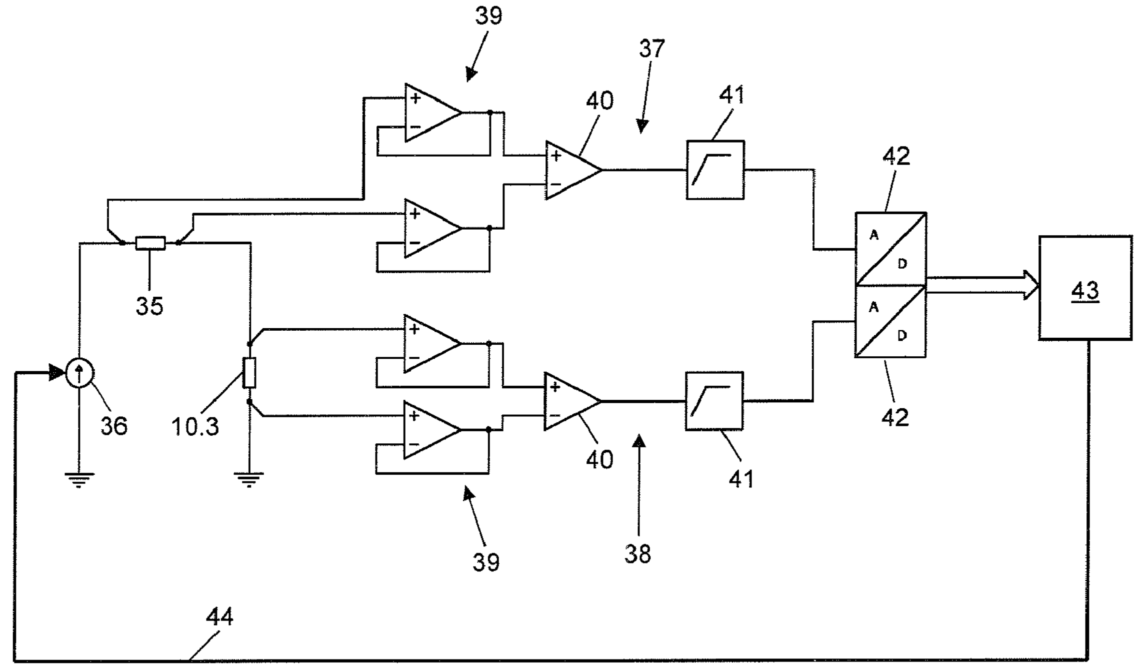
FIG. 14 is a diagrammatically simplified circuit diagram of an electronic measuring and heating system.

FIG. 14 is an equivalent circuit diagram of a measuring and control unit for heating and for measuring the heating current by means of the meandering heating/measuring structure or heating conductor. The equivalent circuit diagram shows the heating/measuring structure 10.3 as a resistor connected in series with a current measuring resistor 35 and a controllable power source 36. The voltages at the current measuring resistor 35 and at the heating/measuring structure 10.3 are picked off by means of separate measuring channels 37, 38. The two measuring channels 37, 38 are identical, each comprising an impedance converter 39 consisting of two operational amplifiers, an operational amplifier 40 for amplifying the measuring signal, an anti-aliasing filter 41 and an A/D converter 42 converting the analogue measuring signal to a digital value. The two measuring channels 37, 38 are therefore high-impedance components and identical in design.

The operational amplifiers 40 of the two measuring channels 37, 38 are preferably operational amplifiers with laser-trimmed internal resistance and an amplification which is adjustable very precisely. In the illustrated embodiment, the operational amplifier LT 1991 produced by Linear Technology is used. The two A/D converters 42 of the two measuring channels 37, 38 are preferably implemented as a synchronous two-channel A/D converter covering both channels simultaneously. This ensures that the measured values of the two channels are always scanned at the same time. As a result, the voltages at the current measuring resistor and at the heating element or at the heating/measuring structure 10.3 are picked off simultaneously and are therefore based on the heating or measuring current flowing through the current measuring resistor 35 or the heating/measuring structure 10.3 respectively.

As the heating and measuring current is measured, it can be used at one and the same time for heating and measurement. With conventional measuring devices, a constant measuring current which is not measured at the sensor is fed in. Such a measuring current can however not be varied and changed for heating, so that heating and measurement have to be carried out independently.

As heating and measurement run concurrently with a heating and measuring current, the temperature can be controlled more precisely.

The temperature is measured at a high scanning rate of, for example, more than 1000 Hz, preferably at least 3000 Hz. This permits an extremely precise temperature adjustment. It has been found that a heating rate of 85° C./s can be controlled with an accuracy of 0.1° C. with just under 3000 Hz.

In the cooling process, a heating and measuring current of approximately 50 mA flows, and when maintaining a temperature this current is 350 mA to 400 mA.

As the heating/measuring structure 10.3 is designed as a long, thin and narrow conductor, a sufficiently high resistance is obtained even when using copper; this can be scanned reliably using the above 4-point measurement even if the heating current is low. 4-point measurement is independent of parasitic resistances. This is due to the fact that, as the heating/measuring structure 10.3 according to the invention is used both as a heating element and as a measuring resistor for measuring the heating voltage, it is impossible to apply randomly high "measuring currents" to the heating/measuring structure 10.3, because these measuring currents also act as heating currents and would result in a significant temperature increase, which is not always desirable. We therefore have marginal conditions which, in certain process conditions, require a very low measuring current to avoid an undesirable temperature change in the reaction chamber. As two identical measuring channels 37, 38 are used, which simultaneously pick off the measuring voltage with a very high impedance and measure it with very precise amplifiers, even minor voltage drops at the resistors 35 and 10.3 can be detected reliably. As the measuring channels are identical, systematic measuring errors cancel each other, because the resistance R measured at the heating/measuring structure 10.3 is the quotient of heating current and heating voltage or of the two measuring signals.

The heating/measuring structure 10.3 is formed on the side of the flexible PCB 10 which is remote from the biochip 6. The opposite side of the flexible PCB supports the continuous temperature homogenisation layer 21, which results in an even and fast heat distribution and a correspondingly even and fast heating of the biochip 6. In addition, the flexible PCB has a thermal capacity of only approximately 12 mJ/K, which results in a fast transfer of the generated heat to the sample fluid and the biochip in the reaction chamber.

Comparable conventional heating devices are usually based on conductors of a material with a higher resistivity than copper, such as NiCr, and separate conductors are provided for heating and measurement, as it has been found difficult to heat and to measure temperature with a single copper conductor. Up to now, silicon substrates have been used as heating elements as a rule, as they were thought to ensure a fast heat distribution owing to their high thermal conductivity. The thermal capacity of such silicon substrates, however, is 10 times as high as that of the flexible PCB according to the invention. This slows the heating process down considerably.

The measured values obtained with the circuit described above are fed to a digital control unit 43, which drives the controllable power source 36 via a line 44.

Figure 15:
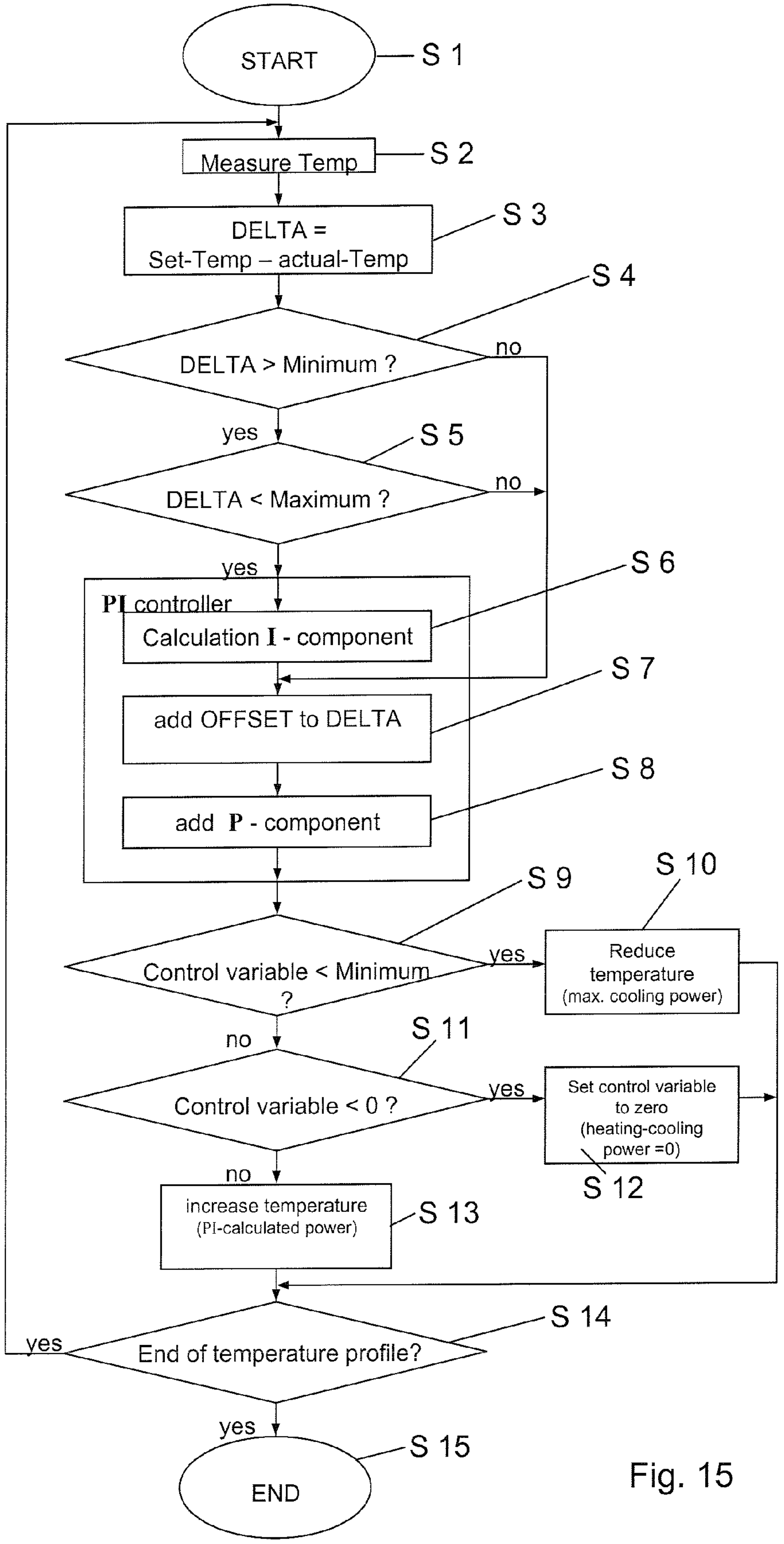
FIG. 15 is a flow chart of an automatic control process.

The automatic control process diagrammatically illustrated in FIG. 15 runs in the control unit 43.

This method for producing a temperature profile begins with step S1. In step S2, the temperature value is measured, i.e. the resistance of the heating/measuring structure 10.3 is calculated from the two measured values and converted into a temperature value in accordance with a table.

Step S3 calculates the difference between the actual measured temperature and a set temperature. This value is identified as delta value. The set temperature changes in the course of time. The function describing this time-variable temperature is the temperature profile to be applied to the reaction chamber.

Step S4 scans whether the delta value exceeds a preset minimum. If the answer is "Yes", the process continues with step S5, which scans whether this delta value is less than a preset maximum. If the answer is once again "Yes", the process continues with a block of steps S6, S7, S8, wherein an integral component of a control value is calculated (step S6), an offset value is added to the delta value (step S7) and a proportional component is calculated on the basis of the changed delta value (step S8). A control variable is obtained by adding the integral component and the proportional component together. As a result of adding the offset value, the heating power is increased.

If the answer to either of the two above scans (step S4 or step S5) is "No", the process continues with step S7, omitting the calculation of the integral component. This means that an integral component is calculated only within a predetermined set temperature range. This range is approximately +/−1° C. to +/2° C. The integral component is therefore used only if the actual measured temperature is relatively close to the desired set temperature. On the one hand, this prevents the overshooting of the actual temperature owing to the very slow-acting integral component. On the other hand, the integral component permits a very precise and fast approximation towards the desired set temperature in the last control phase.

Step S9 checks whether the control variable is less than a preset minimum. If this is the case, the process continues with step S10, in which the temperature is reduced with maximum cooling power.

If step S9 shows that the control variable is not less than a preset minimum, the process continues with step S11, in which it is checked whether the control variable is less than zero. If this is the case, the process continues with step S12, in which the control variable is set to zero. This means that the reaction chamber is cooled without any additional cooling power or that the cooling piston is removed from the reaction chamber. This prevents overshooting.

If, however, the control variable is not found to be less than zero in step S11, this means that the temperature has to be increased. In step S13, the temperature is increased in accordance with the control variable which has been determined. A control signal proportional to the control variable is now fed to the controllable power source 36, which generates a suitable heating current through the heating/measuring structure 10.3.

Step S14 checks whether the end of the temperature profile has been reached. If this is the case, the process is terminated with step S15. If not, the process continues with step S2. This automatic control process is repeated at a scanning frequency of at least 1000 Hz, in particular at least approximately 3000 Hz.

Figure 16:
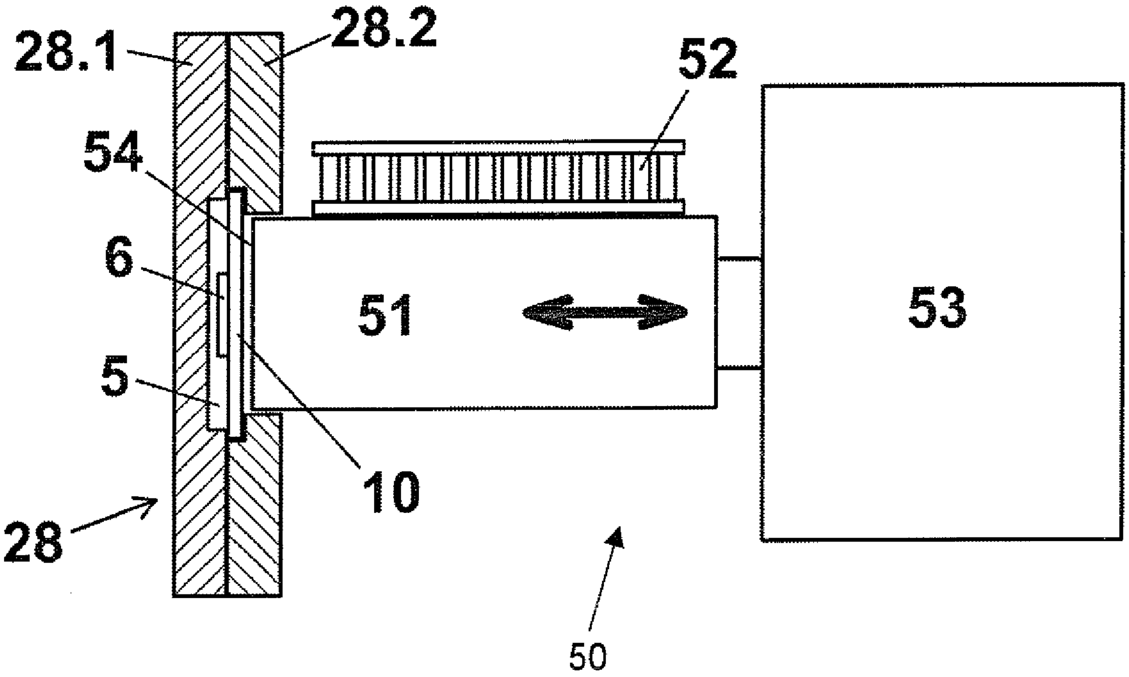
FIG. 16 is a highly simplified diagrammatic representation of a cooling device.

Cooling Device for Temperature-Controlled Biological Test Reactions:

FIG. 16 illustrates the basic principle of the cooling device 50 according to the invention. This cooling device 50 comprises a heat sink hereinafter referred to as the cooling piston 51. The special feature of this cooling piston 51 lies in the fact that it is movable relative to the cartridge 28, so that a cooling surface can be brought into contact with the cartridge 28 to cool the reaction chamber 5 of the cartridge 28. The cooling piston 51 may either be arranged stationary while the cartridge 28 is moved by a linear drive, or the cartridge 28 may be arranged stationary while the cooling piston 51 is moved by means of a linear drive.

The cooling piston 51 is provided with a cooling unit 52 comprising a cooling element in form of a Peltier element, a heat sink and a fan. With this cooling unit 52, the cooling piston 51 can be cooled to a preset temperature. The cooling device 50 further comprises a linear drive 53 for the reciprocating movement of the cooling piston. The cooling piston 51 has an end face hereinafter referred to as the cooling surface 54, which can be brought into contact with the cartridge. The cooling piston 51 is dimensioned such that the cooling surface 54 can be brought into cooling contact with the cartridge or the flexible PCB 10 in the region of the reaction chamber 5.

In contrast to the flexible PCB 10 and the reaction chamber 5, the cooling piston 51 has a very high thermal capacity. In the embodiments described below, the thermal capacity of the cooling piston 51 is approximately 8 to 9 J/K. The total thermal capacity of the reaction chamber 5, on the other hand, is only approximately 0.5 J/K. While this ensures an excellent heat transfer on the one hand, the high thermal capacity of the cooling piston 51 on the other hand means that its temperature is not altered substantially even if the reaction chamber 5 is cooled by a very high temperature differential. As a result, the operating temperature of the cooling piston 51 can be maintained using relatively little cooling power. Owing this high thermal capacity of the cooling piston, the required fast cooling process of the reaction chamber 5 is chronologically uncoupled from the cooling unit 52, which slowly dissipates the heat from the cooling piston 51 to the environment, using relatively little cooling power.

In addition, a relatively low temperature level of e.g. 20° C. can be maintained at the cooling piston 51 compared to the temperatures in the reaction chamber, which allows for fast cooling processes, in particular in PCR reactions, where a temperature of 98° C. is repeatedly reduced to a temperature of 40° C. to 60° C.

At the point in time when the reaction chamber 5 has reached target temperature, or immediately prior to this, the cooling piston 51 is moved away from the reaction chamber 5. A little heat may then be used to stabilise the final temperature. This typically happens if the set temperature is higher than the room temperature. If the temperature falls below the set temperature, automatic heating is triggered. If a temperature lower than room temperature is required in the reaction chamber, which applies to many biological tests, the cooling piston is set to this temperature and permanently pressed against the reaction chamber.

In special applications where a low cooling rate is required, the heating device may be used while the cooling piston 51 is in contact. This is particularly expedient at minor temperature changes up to approximately 40° C. to 50° C. This system can, however, also be used to maintain a temperature below room temperature, where the piston cooled to a temperature below target temperature is in permanent contact with the reaction chamber. A reduced cooling rate can alternatively be achieved by reducing the force with which the cooling piston is pressed against the reaction chamber.

Figure 17:
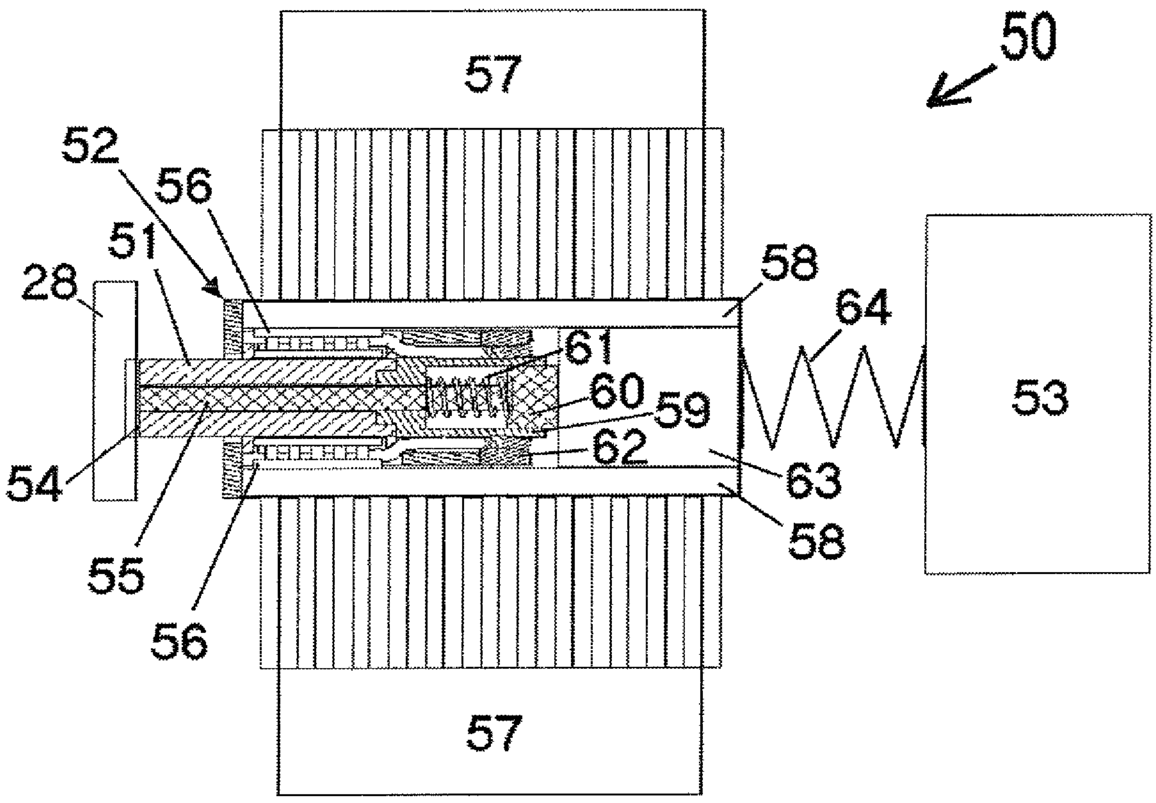
FIG. 17 is a diagrammatically simplified sectional view of a first embodiment of the cooling device.

A first embodiment of the cooling device according to the invention is shown in FIG. 17. This cooling device once again comprises a cooling piston 51, a cooling unit 52 and a linear drive 53.

Suitable linear drives include stepper motors or geared servomotors with spindle or worm gearing, linear stepper motors, piezoelectric linear motors, motors with rack and pinion, rotating magnets, lifting magnets, voice coil magnets, motors with disc cams etc.

The cooling piston 51 has the shape of a cylindrical tube. It is made of metal, for example copper or aluminium. In the interior of the cooling piston 51, a pin- or rod-shaped plunger 55 made of a plastic material or a metal such as copper or aluminium is movably mounted. The plunger 55 is capable of axial displacement in the cooling piston 51. It is as thin as possible, and the end facing the reaction chamber is rounded, so that it applies pressure to a single point of the reaction chamber as far as possible.

The cooling piston 51 is made of metal, because metal has a high thermal conductivity. It may also be made of another material with a high thermal conductivity, such as special ceramics (aluminium oxide ceramics etc.) or plastics with certain fillers, such as graphite, metal powder or tiny metal beads, plastic nano tubes, $Al_2O_3$ ceramic powder.

The end face 54 of the cooling piston 51 which projects from the cooling device 50 acts as a cooling surface 54. In the circumferential region remote from the cooling surface, the cooling piston 51 has two flat surfaces to which cooling elements 56 in the form of Peltier elements are secured. These cooling elements are parts of the cooling unit 52, which further comprises fans 57 and heat sinks 58. The fans 57 are integrated into a housing which accommodates a section of the cooling piston 51.

At the rear end opposite the cooling surface 54, the cooling piston 51 is provided with a bushing 59 made of a material with poor thermal conductivity, such as plastic. This bushing 59 bounds a hollow space. The rear end of the plunger 55 extends into this space with a plug-shaped end body 60 capable of sliding in the bushing 59. Between this end body 60 and the wall of the bushing 59 which bears against the cooling piston 51, a tensioned spring 61 applies a force to the plunger which draws the plunger 55 into the cooling piston 51 by its free end face remote from the end body 60 (part of the cooling surface 54).

The bushing 59 is secured in the housing by means of a plastic ring 62. The housing further accommodates a linear drive 63 to apply a force to the end body 60 or the plunger 55 in order to push a section of its free end out of the cooling piston 51. The whole assembly comprising the cooling piston 51, the plunger 55, the cooling unit 52 and the linear drive 63 is mounted to slide in the axial direction of the cooling piston 51 and coupled to the linear drive 53. The coupling element is a spring 64. This spring has a defined force/displacement characteristic and therefore enables a displacement control on the linear drive 53 to control the force with which the cooling piston 51 is pressed against the flexible PCB 10 without having to control or measure this force using an additional sensor. This type of pressure adjustment meets the requirements of the application, because tolerances relating to the set force are not critical to a large extent.

All exposed and accessible areas of the cooling piston 51 are thermally insulated. A commercially available fine-pored foam material may be provided for this purpose. The cooling surface 54 of the cooling piston 51 is faced and polished. The cooling elements 56 are connected in series and connected to an electronic control unit. In addition, a temperature sensor for measuring the temperature of the cooling piston is provided on the surface of the cooling piston 51. A PI controller is used to control the temperature at the cooling piston 51. The scanning rate for this temperature may for example be 2 Hz.

Owing to the high thermal capacity of the cooling piston 51 and the plunger 55, which is kept cool with the cooling piston 51, the temperature of this two-part cooling body increases by only approximately 2° C. while the temperature of the reaction chamber is reduced by approximately 40° C. The required cooling power is relatively low, being only 1-2 W. As a result, the cooling device can be operated with batteries.

Figure 18:
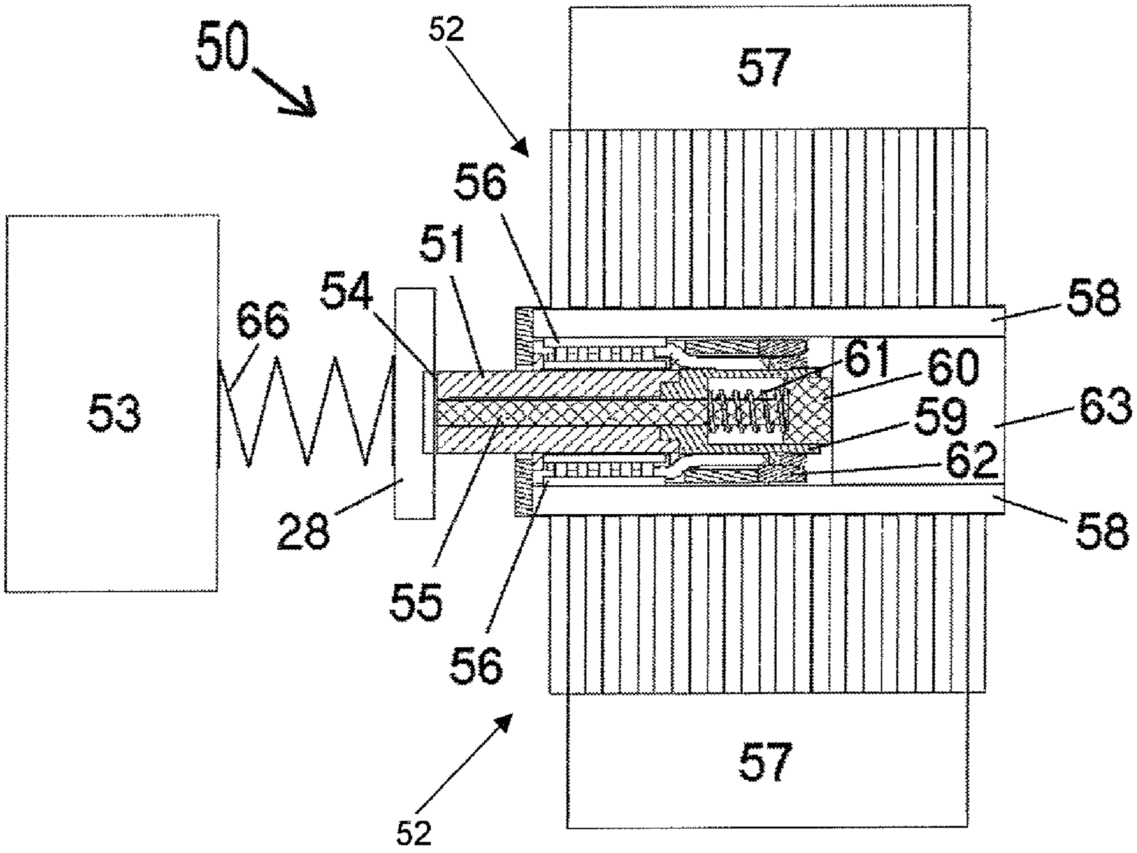
FIG. 18 is a diagrammatically simplified sectional view of a second embodiment of the cooling device.

A second embodiment of the cooling device according to the invention is shown in FIG. 18. Identical components of this second embodiment are identified by the same reference numbers as those in FIG. 17.

The cooling device 50 of the second embodiment likewise comprises a cooling piston 51 in the shape of a cylindrical tube with a cooling surface 54, a plunger 55 movably mounted therein, two cooling units 52, each comprising a cooling element 56, a fan 57 and a heat sink 58, a linear drive 63 for the actuation of the plunger 55 and a spring 61 drawing the plunger into the cooling piston 51 by its free end.

The second embodiment of the cooling device 50 differs from the first embodiment in that the cooling piston 51 is stationary and a linear drive 65 is provided for moving the cartridge 28. This linear drive 65 is coupled to a holding device (not shown in the drawing) for the accommodation of the cartridge by means of a spring 66. The holding device is supported in a linear manner. The cartridge can be installed into the holding device in a reproducible position. Via the force/displacement characteristic of the spring 66, the force with which the cartridge is pressed against the cooling piston 51, 55 can be adjusted by means of a displacement control.

The linear drives 53, 63 and 65 are designed such that they can be actively retracted in order to change the cartridge.

This device offers the advantage that only the cartridge 38, which is relatively small compared to the rest of the cooling device, is moved.

To obtain certain temperature profiles with a minimum temperature exceeding room temperature by approximately 10° C. to 20° C., active cooling is not required. All that is required for this purpose is the provision of a cooling unit in the form of cooling fins or the like on the cooling piston, to which the heat absorbed by the cooling piston is transferred by convection and radiation.

The cooling rates of such devices are by necessity lower than in the case of active cooling, but a cooling unit of this type would meet the requirements of many temperature cycles used in practical applications. Other systems can be used as cooling units either individually or in combination, for example water cooling or the generation of very cold air by means of a vortex tube, which is then blown against the cooling piston.

Figure 19:
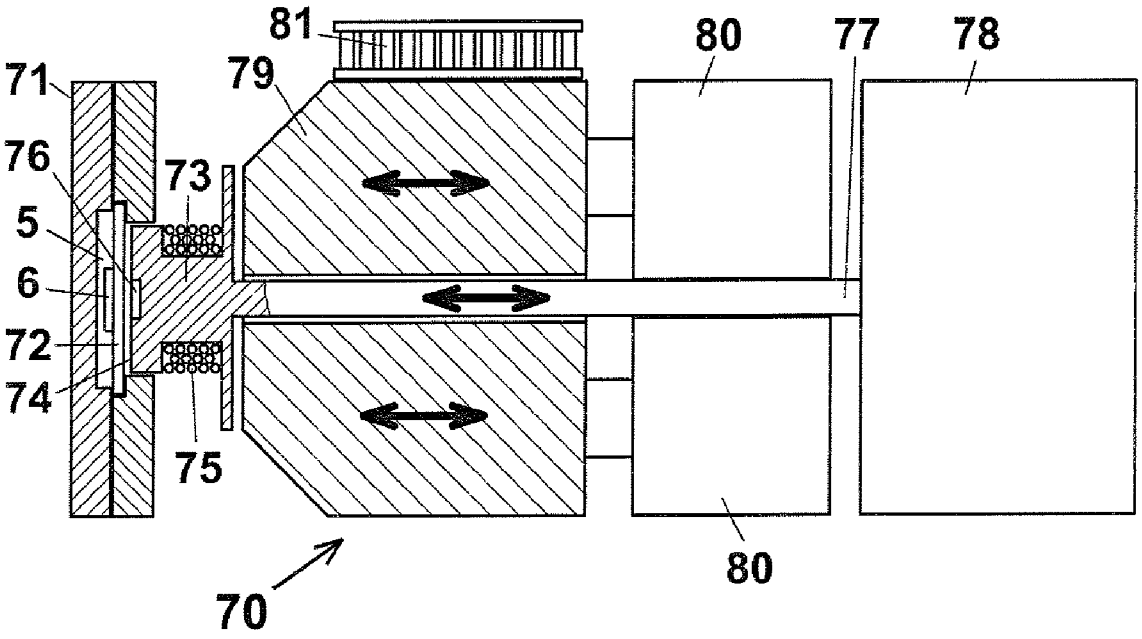
FIG. 19 shows an alternative heating/cooling device for heating and cooling the reaction chamber.
Figure 20:
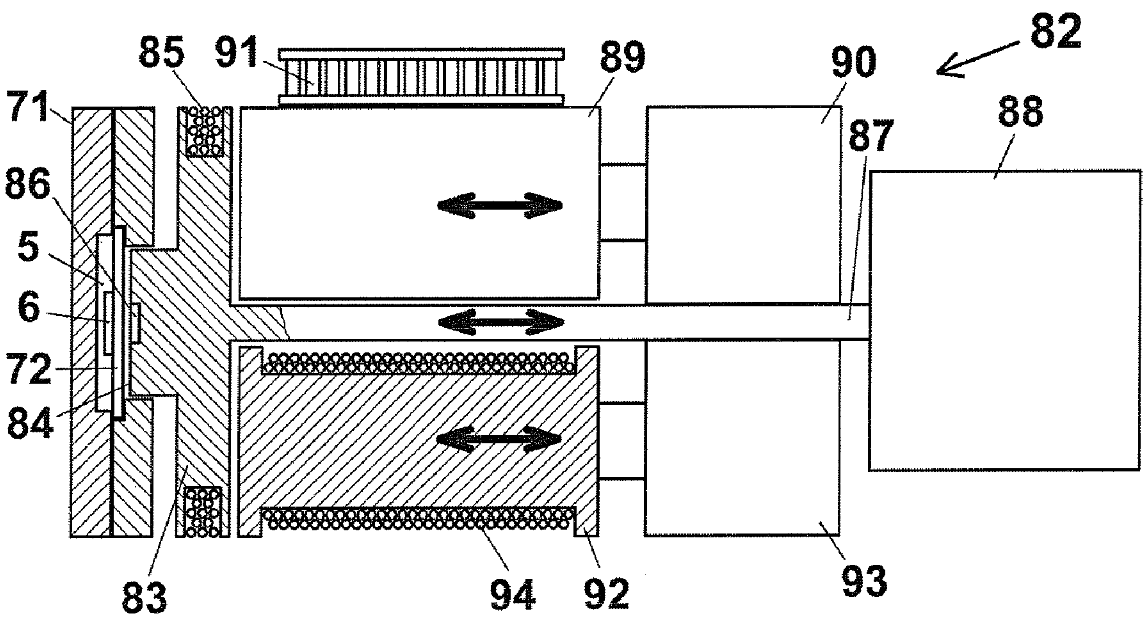
FIG. 20 shows a variant of the heating/cooling device from FIG. 19.

Combined Heating/Cooling Device:

FIGS. 19 and 20 show combined heating/cooling devices for heating and cooling the reaction chamber 5 of the cartridge 28 or of another cartridge 71, which likewise comprises a reaction chamber 5 for a biochip 6, but is not provided with heating means of its own. A region of the reaction chamber 5 is bounded by a thin plate 72 made of a material with good thermal conductivity, which may be flexible. The side of the plate 72 which is remote from the reaction chamber is exposed and can be contacted by the heating/cooling device 70.

The heating/cooling device 70 comprises a heating piston 73 with a contact surface 74 facing the plate 72. The heating piston 73 is made of metal and provided with heating means 75, such as heating wires wound round the heating piston 73. The heating means 75 are connected to a control unit (not shown in the drawing) by means of which the heating piston can be heated to a preset temperature. A temperature sensor 76 on the contact surface 74 detects the temperature of the contact surface 74. The temperature sensor is also connected to the control unit, enabling it to control the temperature of the heating piston 73. Via a shaft 77, the heating piston 73 is joined to a linear drive 78, which can move the heating piston 73 towards the plate 72 until it contacts the latter with a preset pressure, or which can withdraw it from the plate 72 of the cartridge 71 to create a preset air gap between the heating piston 73 and the plate 72.

A cooling piston 79 is movably mounted on the shaft 77 and encloses the shaft 77. The cooling piston 79 is made of metal and displaceable in the longitudinal direction of the shaft 77. The cooling piston 79 is connected to a further linear drive 80, by means of which the position of the cooling piston 79 on the shaft 77 can be adjusted. The linear drive 80 can move the cooling piston 79 towards the heating piston 73 until the cooling piston 79 bears against the heating piston 73 on the side remote from the contact surface 74. In addition, the cooling piston 79 can be removed from the heating piston 73 to create an air gap in between. The cooling piston 79 supports a cooling unit 81 with a Peltier element, a heat sink and a fan in order to cool the cooling piston to a preset temperature.

The mass and volume of the cooling piston 79 significantly exceed those of the heating piston 73. As a result, the cooling piston 79 has a much higher thermal capacity than the heating piston 73. When the cooling piston 79 now contacts the heating piston 73, this combined piston is thermally dominated by the cooling piston and cools the reaction chamber. The heating piston 73 has a low mass and volume and can therefore be heated to preset temperatures using very little energy.

The cooling piston 79 is kept at a comparatively low temperature by means of the cooling unit 81.

If a preset temperature cycle is to be completed with this heating/cooling device, the heating piston 73 is pressed against the plate 72 of the cartridge 71 in the heating phases. In this position, the cooling piston 79 is at a distance from the heating piston 73. The heating piston 73 is heated by its heating means 75 until the desired temperature is set at the interface between the contact surface 74 and the plate 72.

In the cooling phases, the heating means 75 are switched off and the cooling piston 79 is pressed against the heating piston 73 by the linear drive 80. The heating piston 73 is once again in contact with the plate 72 of the cartridge 71. Owing to the fact that the thermal capacity of the cooling piston 79 substantially exceeds that of the heating piston 73, heat is extracted very quickly from the heating piston 73, so that the heating piston is cooled and serves as a cooling means for the reaction chamber 5 of the cartridge 71. During the cooling phase, too, the temperature at the interface between the heating piston 73 and the plate 72 is monitored by the temperature sensor 76. As soon as the desired temperature is obtained, both the heating piston 73 and the cooling piston 79 are retracted by the linear drive 78, or alternatively only the cooling piston 79 is retracted while the heating piston 73 is supplied with heat by the heating means 75, if the temperature of the reaction chamber has to be kept above room temperature. If the temperature of the reaction chamber has to be kept below room temperature, it may be expedient to maintain the contact between the heating piston 73 and the reaction chamber 5 while having the cooling piston 79 contact the heating piston 73. By supplying energy from the heating means 75, the flow of heat from and to the reaction chamber 5 can be controlled such that its temperature remains constant.

The contact surface between the heating piston 73 and the cooling piston 79 is advantageously as large as possible, because this allows a strong heat flow.

A second embodiment of the heating/cooling device 82 is shown in FIG. 20. This second embodiment is slightly different from the embodiment shown in FIG. 19. It is likewise provided for contact between a cartridge 71 with a plate 72 and a heating piston 83 with a contact surface 84. The heating piston 83 is once again provided with heating means 85 and a temperature sensor 86 on the contact surface 84. The heating piston 83 is mounted on a shaft 87 connected to a first linear drive 88, which can bring the heating piston into contact with the plate 72 and remove it therefrom. The shaft 87 supports a movable cooling piston 89, which is in turn connected to a linear drive 90, so that the cooling piston 89 can be brought into contact with the heating piston 83. The cooling piston 89 supports a cooling unit 91 for cooling the cooling piston 89 to a preset temperature and for maintaining this temperature. The shaft 87 further supports an auxiliary heating piston 92, which is movable in the axial direction. The auxiliary heating piston 92 is connected to a further linear drive 93, so that the auxiliary heating piston 92 can be brought into contact with the heating piston 83 or removed therefrom. The auxiliary heating piston 92 is provided with heating means 94 such as wound heating wires for heating to a preset temperature.

The volume and the mass of the cooling piston 89 and the auxiliary heating piston 92 respectively exceed those of the heating piston 83. In a heating or cooling phase, the auxiliary heating piston 92 or the cooling piston 89 respectively is brought into contact with the heating piston 83 in order to heat or cool the heating piston 83 quickly to a preset temperature. Apart from this aspect, this combined heating/cooling device 82 is identical in its operation to the heating/cooling device 70 shown in FIG. 19.

These two heating/cooling devices can be provided with a plunger (not shown in the drawing) extending through the shafts 77 and 87 respectively and capable of applying pressure to the plate 72, if flexible, in order to push the biochip against a detection window opposite (not shown in the drawing).

These two combined heating/cooling devices are preferably used with a cartridge 71 provided with a rigid plate 72 of a material with good thermal conductivity in order to provide a fast transfer of heat between the reaction chamber and the heating piston. The detection window located opposite the plate 72 is elastic, and the detection device (not shown in the drawing) is pressed against the detection window with a transparent plate for reading the biochip, so that the detection window contacts the biochip 6. This displaces the sample fluid between the biochip 6 and the detection window, allowing the reliable scanning of the individual spots of the biochip. A detection window of this type may be made of a transparent, elastic plastic material.

Figure 6:
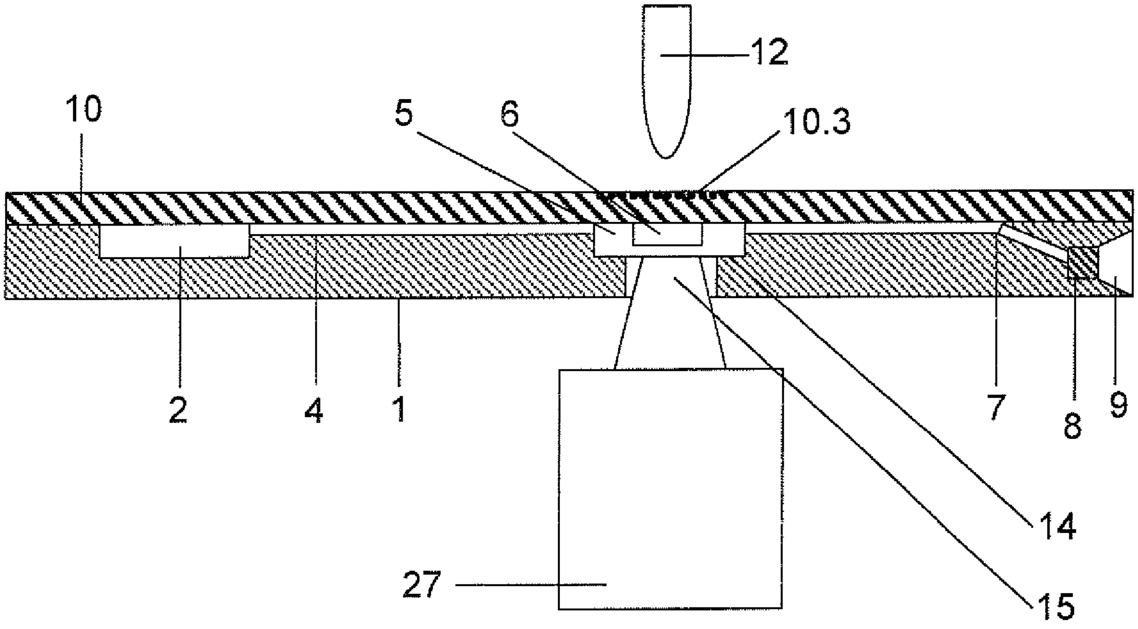
FIG. 6 shows an embodiment of the arrangement of the inlay according to the invention with the associated optical module.

Image Recording:

Following the temperature-controlled biological test reaction, the flexible PCB of a cartridge with a flexible PCB 10 is elastically deformed by the pressure of the plunger 55, so that the biochip bonded thereto presses against the detection surface (FIG. 6). To overcome the air pressure in the equalization chamber 2, a force $F_0$ has to be applied. With an area of approximately 0.5 $cm^2$, only approximately 5 N are required to build up a pressure of 1 bar. In addition, a defined force $F_1$ has to be applied in order to deform the flexible PCB 10 with the mounted biochip 6 by means of the plunger 55, so that the biochip 6 is evenly pressed against the detection surface. The sum of the forces $F_0+F_1$ should not exceed 30 N.

As the plunger is operated, the sample fluid containing pigment molecules, i.e. the surplus fluid between the biochip and the detection surface, is displaced. It flows through the equalization passage 4 into the equalization chamber 2. A lighting unit of an optical module (not shown in the drawing) only causes the pigment molecules still adhering to the biochip to fluoresce. After the operation of the plunger, the lighting and detection unit of the optical module only detects the fluorescent light of the pigment molecules adhering to the biochip. A suitable optical module is described in PCT/EP2007/054823, to which this specification refers.

Figure 9:
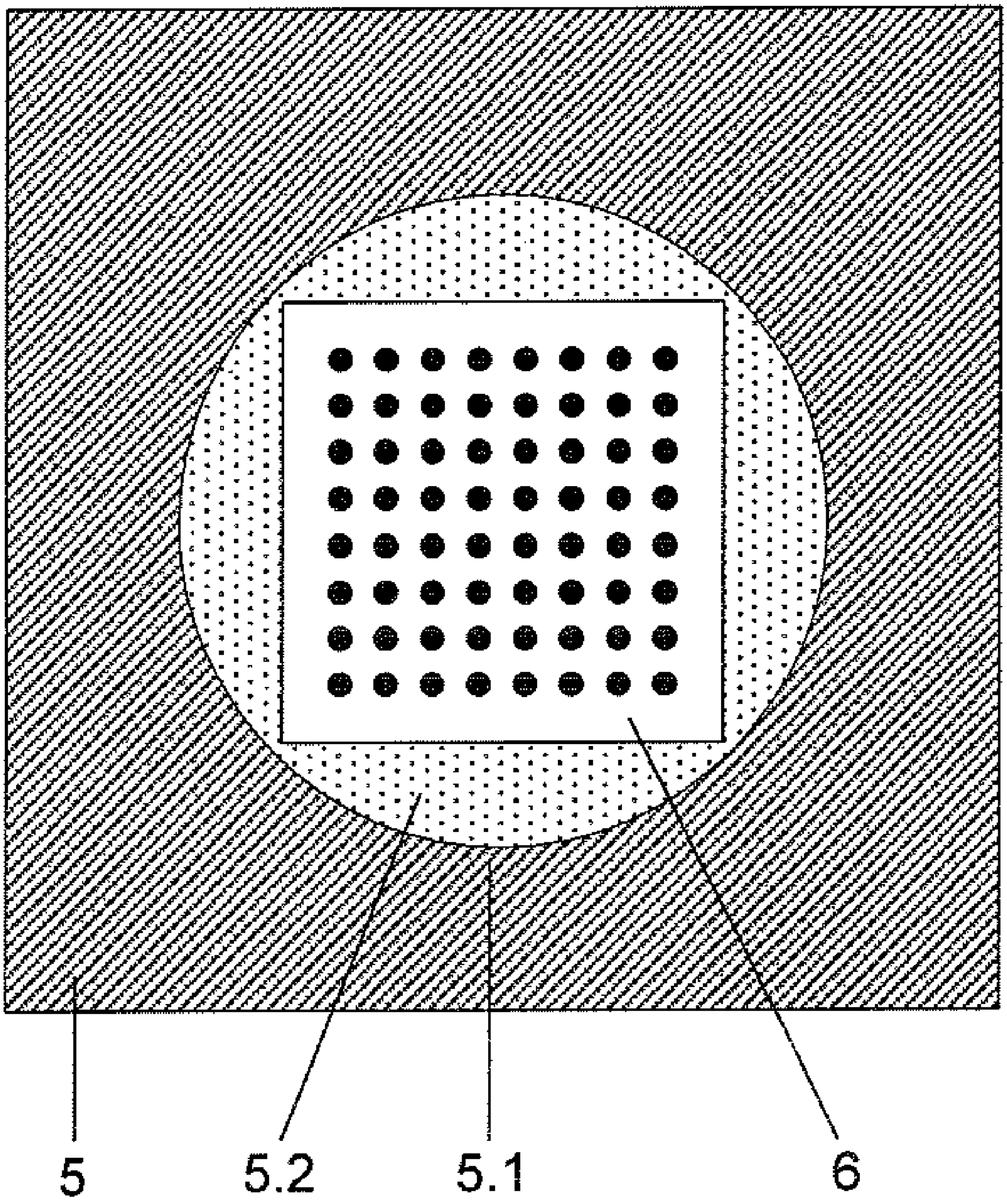
FIG. 9 shows the section of the illuminated surface in the sample space of the inlay without aperture.
Figure 10:
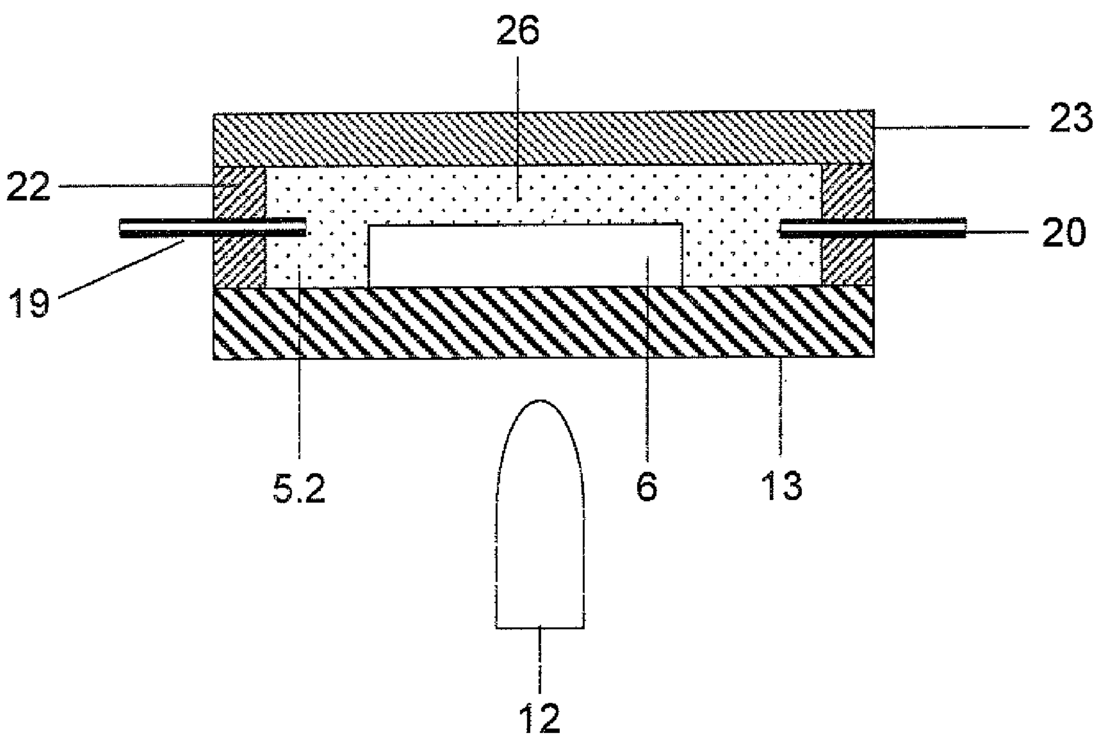
FIG. 10 shows the principle of the method for filling the reaction chamber with a sample fluid through cannulas according to prior art.
Figure 11:
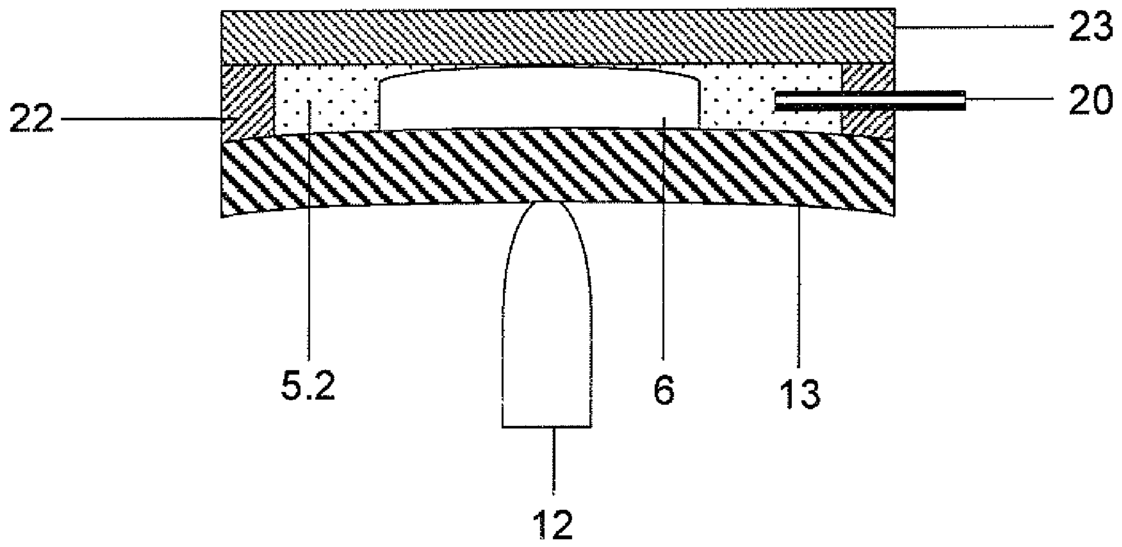
FIG. 11 shows the principle of the method for displacing surplus fluid by means of plungers according to prior art.

Without any special aperture in the optical module, the illumination of the biochip in the reaction chamber is circular. Not only the rectangular biochip 6 is illuminated, but also regions 5.1 of the reaction chamber adjacent to the biochip, where a pigment-containing sample fluid has not been displaced (FIG. 9). These regions fluoresce intensively. In the formation of an image of the biochip on a detector by the optical module, these regions appear outside the biochip, but owing to the high concentration of pigment in the sample fluid adjacent to the biochip, a part of the fluorescent light spreads towards the biochip and onto the reaction fields (spots). In addition to the fluorescent radiation of the spots caused by direct illumination, the detector also detects the indirect fluorescent stray radiation from the regions adjacent to the biochip. As a result, the image of the spots on the biochip receives a local, inhomogeneous background illumination which interferes with image evaluation.

By means of a rectangular aperture 18, 19, which is fitted to the base body above the reaction chamber 5 or integrated therewith and which has geometrical dimensions which are slightly less than those of the biochip (FIG. 7, 8), the optical fluorescence stimulation of the pigment in the reaction chamber adjacent to the biochip is prevented.

Figure 7:
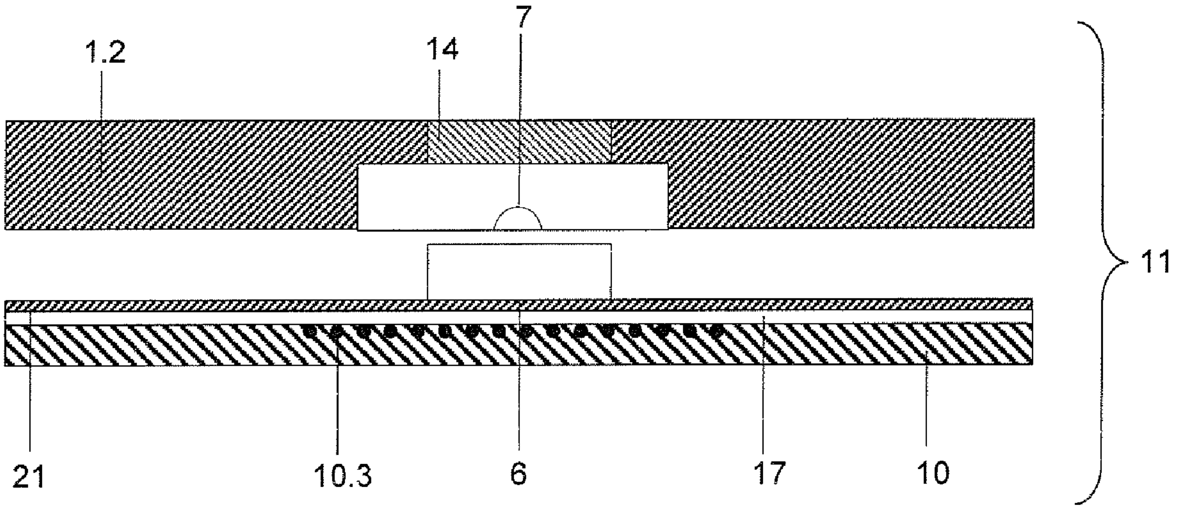
FIG. 7 shows an embodiment of the arrangement according to the invention, equipped with a transparent aperture in an opaque base body.
Figure 8:
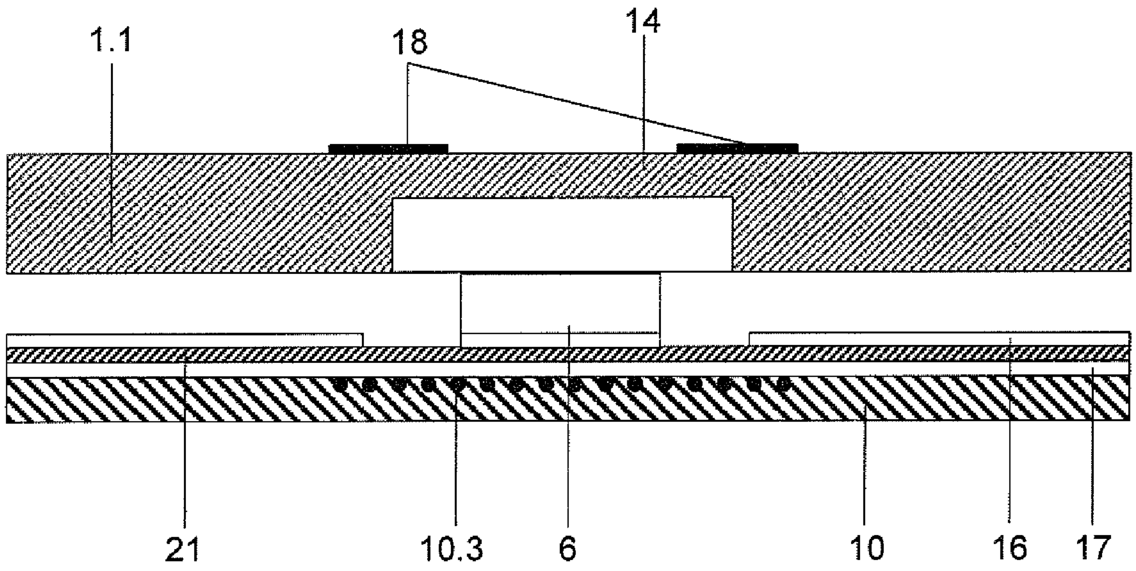
FIG. 8 shows an embodiment of the cartridge according to the invention, equipped with an opaque aperture on a transparent base body.

In the injection moulding process of a transparent base body 1, this aperture 18 can be incorporated as an optically absorbent aperture (FIG. 8), in the injection moulding process of a non-transparent base body as a transparent optical aperture 19 or detection window 14 (FIG. 7). Alternatively, the aperture can be applied to the optical observation window (detection surface) at a later date.

The transmission of the aperture layer should be less than $10^{-2}$.

Repeated Execution of Temperature-Controlled Biological Test Reactions:

In contrast to known devices (e.g. DE 10 2004 022 263 A1), wherein the sample fluid is irreversibly displaced from a reaction chamber by the operation of the plunger before images are recorded, the cartridge 28 according to the invention allows for the continuation of the temperature-controlled biological test reaction after recording. If the plunger 55 is retracted, the flexible PCB 10 is returned to its original position by the positive pressure in the reaction chamber 5 and in the equalization chamber 2, and the sample fluid flows back from the equalization chamber 2 into the reaction chamber 5, including the space between the biochip and the cover glass. The temperature-controlled biological test reaction can therefore continue after the detection process.

With the cartridge according to the invention, the spots on the biochip can in principle be detected at any time during the biological reaction.

Reading and Writing of Data:

All information on the cartridge, including the biochip, has to be read out from the biochip reader. For selecting exact temperatures when running the temperature-controlled biological test reaction, specific calibration data of the heating device on the flexible PCB are required for the respective flexible PCB. Information on the reaction fields (spots) on the biochip, on ID numbers, on exposure times for image recording etc. also have to be read from the reader in order to control the temperature-controlled biological test reaction and to allow data logging and filing.

The necessary information can be applied to the cartridge as a dot code or bar code. A dot code (or bar code) reader is required to read these codes. Current data cannot be stored.

A more flexible solution is the use of writeable and readable tamper-proof storage media 10.2, which are advantageously integrated onto the flexible PCB.

Adjacent to the contact surfaces 10.1 of the heating/measuring structure, an electrically programmable non-volatile memory can be contacted on the flexible PCB (FIG. 3). This enables data to be stored digitally and to be retrieved at any time. In this case, the storable data volume is significantly larger than when applying bar or dot codes.

With a contacted, electrically programmable non-volatile memory, information can be stored even during the PCR process or while reading the biochip. The data can moreover be stored in a tamper-proof manner. After processing, the cartridge can be marked as "processed" in order to avoid any inadvertent repeat processing.

LIST OF REFERENCE NUMBERS

1 Base body
1.1 Transparent base body
1.2 Non-transparent base body
2 Equalization chamber
3 Window
4 Equalization passage
5 Reaction chamber
5.1 Illuminated area
6 Biochip
6.1 Reaction fields (spots)
6.2 Rear coating
7 Filling passage
8 Check valve
9 Filling port
10 Flexible PCB
10.1 Contact surfaces of flexible PCB
10.2 Storage medium
10.3 Heating/measuring structure of flexible PCB
11 Inlay
12 Plunger
13 Membrane
14 Detection window
16 Adhesive bonding layer
17 Backing layer
18 Aperture (non-transparent)
19 Filling cannula
20 Pressure balancing cannula
21 Temperature homogenisation layer
22 Seal
23 Cover glass
24 Stabilising plate
25 Cartridge base body
26 Sample fluid
27 Optical module
28 Cartridge
28.1 Upper part of cartridge housing
28.1 Lower part of cartridge housing
29.1 Recess in 28.1
29.2 Recess in 28.2
30.1 Heating current
30.2 Heating current
31.1 Measuring current
31.2 Measuring current
32 Conductor
33 Contact point
34 Contact point
35 Current measuring resistor
36 Power source
37 Measuring channel
38 Measuring channel
39 Impedance converter
40 Operational amplifier
41 Anti-aliasing filter
42 A/D converter
43 Control unit
44 Line
50 Cooling device
51 Cooling piston
52 Cooling unit
53 Linear drive
54 Cooling surface
55 Plunger
56 Cooling element
57 Fan
58 Heat sink
59 Bushing
60 End body
61 Spring
62 Plastic ring
63 Linear drive
64 Spring
65 Linear drive
66 Spring
70 Heating/Cooling device
71 Cartridge
72 Plate
73 Heating piston
74 Contact surface
75 Heating means
76 Temperature sensor
77 Shaft
78 Linear drive
79 Cooling piston
80 Linear drive
81 Cooling unit
82 Heating/cooling device
83 Heating piston
84 Contact surface
85 Heating means
86 Temperature sensor

87 Shaft
88 Linear drive
89 Cooling piston
90 Linear drive
91 Cooling unit
92 Auxiliary heating piston
93 Linear drive
94 Heating means

The invention claimed is:

1. A cartridge comprising an equalization chamber, an equalization passage and heated reaction chamber for processing a biochip, the heated reaction chamber communicating with the equalization chamber via the equalization passage, the equalization passage comprising a window, and the heated reaction chamber comprising:

(a) a flexible printed circuit board forming a boundary wall of the reaction chamber, wherein a conductor serving as a heating device is formed on the flexible printed circuit board, and (b) a measuring and control unit connected to the conductor serving as a heating device, the measuring and control unit designed to control the conductor serving as a heating device both for heating and for measuring the temperature, wherein the measuring and control unit is designed for simultaneous heating and measuring the temperature.

2. The cartridge of claim 1, wherein the measuring and control unit comprises two substantially identical measuring channels designed to measure the heating voltage and the heating current.

3. The cartridge of claim 2, wherein each of the two measuring channels is provided with an A/D converter forming a part of a synchronous two-channel A/D converter.

4. The cartridge of claim 1, wherein the measuring and control unit is connected to pick off the voltage at the heating conductor and the voltage at a current measuring resistor connected in series with the heating conductor.

5. The cartridge of claim 1, wherein the measuring and control unit is designed for scanning the temperature with a scanning rate of at least 1000 Hz.

6. The cartridge of claim 1, wherein the measuring and control unit is designed for scanning the temperature with a scanning rate of at least 3000 Hz.

7. The cartridge of claim 4, wherein the measuring and control unit is designed for scanning the temperature with a scanning rate of at least 1000 Hz.

8. The cartridge of claim 4, wherein the measuring and control unit is designed for scanning the temperature with a scanning rate of at least 3000 Hz.

9. The cartridge of claim 1, wherein the heating conductor is located on the side of the flexible printed circuit board which is remote from the reaction chamber, and wherein a temperature homogenization layer of a thermally conductive material is provided on the side of the flexible printed circuit board which faces inwards towards the reaction chamber.

10. The cartridge of claim 7, wherein the heating conductor is located on the side of the flexible printed circuit board which is remote from the reaction chamber, and in that a temperature homogenization layer of a thermally conductive material, is provided on the side of the flexible printed circuit board which faces inwards towards the reaction chamber.

11. The cartridge of claim 1, wherein the heating conductor does not have any crossovers.

12. The cartridge of claim 1, wherein the heating conductor has a resistance of about 5 to 100 ohms at room temperature.

13. The cartridge of claim 1, wherein the heating conductor has a resistance of about 5 to 100 ohms at room temperature.

14. The cartridge of claim 1, wherein the heating conductor is made of copper.

15. The cartridge of claim 1, wherein a semiconductor memory for storing data specific to the respective reaction chamber is provided on the flexible printed circuit board and connected to a control unit for controlling the heating and measuring current via conductors.

16. The cartridge of claim 1, wherein the biochip is connected to the flexible printed circuit board in the region of the heating conductor.

17. The cartridge of claim 16, wherein the heating conductor extends across a region which is larger than the biochip.

18. The cartridge of claim 1, wherein the cartridge is provided with a filling port including a check valve, and wherein the filling port communicates with the reaction chamber by means of a filling passage.

19. The cartridge of claim 18, wherein a self-contained communicating fluid passage is provided between the filling port and the equalization chamber.

20. The cartridge of claim 1, further comprising a cooling device equipped with a cooling piston which can be brought into contact with the reaction chamber in order to cool it.

21. The cartridge of claim 19, further comprising a cooling device equipped with a cooling piston which can be brought into contact with the reaction chamber in order to cool it.

22. The cartridge of claim 20, wherein the cooling device comprises a drive for the automatic movement of the cooling piston, wherein the drive enables the cooling piston to contact the flexible printed circuit board with a cooling surface.

23. A method for controlling a heated reaction chamber for processing a biochip, comprising providing a cartridge comprising an equalization chamber, an equalization passage and a reaction chamber, the reaction chamber communicating with the equalization chamber via the equalization passage, the equalization passage comprising a window, wherein the reaction chamber comprises a flexible printed circuit board forming a boundary wall of the reaction chamber, wherein a conductor serving as a heating device is formed on the flexible printed circuit board, and wherein a current for simultaneous heating and temperature measurement is made to flow through the conductor serving as a heating device in a heating phase.

24. The method of claim 23, wherein the temperature is measured with a scanning rate of at least 1000 Hz.

25. The method of claim 23, wherein the temperature is measured with a scanning rate of at least 3000 Hz.

26. The method of claim 23, wherein a proportional-integral controller is used within a preset temperature interval about a set temperature and a proportional controller is used outside the preset temperature interval.

27. The method of claim 23, wherein a control variable is determined from the difference between a set temperature and an actual temperature, wherein, when the control variable is less than a preset minimum, the cooling piston is pressed against the reaction chamber.

28. The method of claim 27, wherein if the control variable is less than zero and more than the minimum, the cooling piston is set at a distance from the reaction chamber.

29. The method of claim 27, wherein the reaction chamber is heated if the control variable is more than zero.

* * * * *